United States Patent
Mandel et al.

(10) Patent No.: US 10,933,016 B2
(45) Date of Patent: Mar. 2, 2021

(54) COMPOSITIONS AND METHODS FOR ORAL ADMINISTRATION OF CANNABINOIDS AND TERPENOIDS

(71) Applicant: TRINIDAD CONSULTING, LLC, Arcata, CA (US)

(72) Inventors: Case Michael Mandel, Trinidad, CA (US); Clifton Anton Sammet, Trinidad, CA (US)

(73) Assignee: TRINIDAD CONSULTING, LLC, Arcata, CA (US)

( * ) Notice: Subject to any disclaimer, the term of this patent is extended or adjusted under 35 U.S.C. 154(b) by 208 days.

(21) Appl. No.: 15/904,356

(22) Filed: Feb. 24, 2018

(65) Prior Publication Data

US 2019/0060225 A1    Feb. 28, 2019

Related U.S. Application Data

(60) Provisional application No. 62/463,151, filed on Feb. 24, 2017.

(51) Int. Cl.

| | | |
|---|---|---|
| *A61K 9/00* | (2006.01) | |
| *A61K 36/185* | (2006.01) | |
| *A61K 47/44* | (2017.01) | |
| *A61K 47/06* | (2006.01) | |
| *A61K 47/46* | (2006.01) | |
| *A61K 47/38* | (2006.01) | |
| *A61K 31/235* | (2006.01) | |
| *A23L 33/105* | (2016.01) | |
| *A61K 31/352* | (2006.01) | |
| *A61K 47/24* | (2006.01) | |
| *A61K 47/36* | (2006.01) | |
| *A61K 47/42* | (2017.01) | |

(52) U.S. Cl.
CPC .......... *A61K 9/0056* (2013.01); *A23L 33/105* (2016.08); *A61K 9/009* (2013.01); *A61K 31/235* (2013.01); *A61K 31/352* (2013.01); *A61K 36/185* (2013.01); *A61K 47/06* (2013.01); *A61K 47/24* (2013.01); *A61K 47/36* (2013.01); *A61K 47/38* (2013.01); *A61K 47/42* (2013.01); *A61K 47/44* (2013.01); *A61K 47/46* (2013.01); *A23V 2002/00* (2013.01)

(58) Field of Classification Search
CPC .. A61K 31/235; A61K 31/352; A61K 36/185; A61K 9/009; A61K 47/38; A61K 47/36; A61K 31/05; A61K 9/0056
See application file for complete search history.

(56) References Cited

U.S. PATENT DOCUMENTS

| | | | |
|---|---|---|---|
| 5,847,128 A | 12/1998 | Martin | |
| 7,025,992 B2 | 4/2006 | Whittle | |
| 7,186,850 B2 | 3/2007 | Silverberg | |
| 8,906,429 B1 | 12/2014 | Kolsky | |
| 9,526,792 B1 | 12/2016 | Degeeter | |
| 9,974,739 B2 | 5/2018 | Riello | |
| 2004/0138293 A1 | 7/2004 | Werner | |
| 2008/0064679 A1* | 3/2008 | Martin | C07D 405/06 514/212.01 |
| 2014/0271940 A1 | 9/2014 | Wurzer | |
| 2016/0199299 A1 | 7/2016 | Uren | |
| 2016/0296464 A1* | 10/2016 | Lindsay | A61K 9/009 |

FOREIGN PATENT DOCUMENTS

| | | | | |
|---|---|---|---|---|
| GB | 2524207 A | | 9/2015 | |
| WO | WO 2016/099960 | * | 6/2016 | ............. A24F 23/02 |
| WO | PCT/US2017/067135 | | 2/2018 | |

OTHER PUBLICATIONS

Wiebelhaus et al. (Differentiation of marijuana headspace volatiles from other plants and hemp products using capillary microextraction of volatiles (CMV) coupled to gas-chromatography-mass spectrometry (GC-MS), Forensic Chemistry 2 (2016), 1-8).*

Russo (Taming THC: potential cannabis synergy and phytocannabinoid-terpenoid entourage effects, British Journal of Pharmacology (2011), 163, 1344-1364).*

Juntunen et al., Anandamide prodrugs: Water-soluble phosphate esters of arachidonylethanolamide and R-methanandamide, European Journal of Pharmaceutical Sciences, vol. 19, Issue 1, 2003, pp. 37-43.

* cited by examiner

*Primary Examiner* — Kortney L. Klinkel
(74) *Attorney, Agent, or Firm* — Rimôn, P.C.

(57) ABSTRACT

The present invention relates to oral administration of water soluble cannabinoid and terpenoid concentrates on a flavored fibrous carrier. The compositions described herein provide an alternative to smoked cannabis that also avoid the slow action and unpredictable dosing of edible cannabis preparations. Water soluble concentrates of cannabinoids and terpenoids may be produced by derivatization reactions which are known in the art. Such water soluble concentrates enjoy significantly increased absorption by mucosal membranes of the mouth and may therefore be experienced by the consumer more quickly. Water soluble cannabinoid and terpenoid concentrates may be used in combination with each other and in combination with non-derivatized molecules which provides the user with fast and slow acting components in a single delivery vehicle.

6 Claims, No Drawings

COMPOSITIONS AND METHODS FOR ORAL ADMINISTRATION OF CANNABINOIDS AND TERPENOIDS

FIELD OF INVENTION

The market for products containing cannabis and extracts thereof has grown significantly in the wake of widespread medical and recreational legalization. In addition to cannabis flowers which are usually consumed by smoking, there are now a range of cannabis concentrates, a variety of edible products as well as eye drops and transdermal patches to name a few.

BACKGROUND OF THE INVENTION

Many cannabis smokers desire smokeless alternatives because of the cumulative adverse effects of smoking. Until recently the main alternative to smoked cannabis was edible cannabis. However most users of edible cannabis find that it has undesirable characteristics including slow action, often requiring an hour or more before effects are felt, and unpredictable dosing. Ingested cannabinoids are subject to first pass metabolism by the liver which generates metabolites with elevated psychoactivity. These problems are often exacerbated by users who subsequently consume additional quantities in the mistaken belief that their initial dose was inadequate. Therefore what is needed are edible cannabis products without the adverse health effects of smoking that are fast acting and provide a consistent dose.

The recent proliferation of cannabis concentrates has enabled a new generation of orally administered cannabis products which allow for fast action and more consistent absorption. Cannabis concentrates can be produced by a range of methods including mechanical processes, non-polar solvent extraction, alcohol extraction, and high pressure carbon dioxide extraction (super critical fluid extraction) among others. Concentrates produced by these extraction processes can be easily combined with edible ingredients for consistent dosing. Unfortunately the resulting compositions continue to be slow acting because of the low water solubility of cannabinoids. Cannabinoids and the closely related terpenoids consist of combinations of five carbon isoprene units which have strong lipid character and are therefore not readily absorbed into blood until after being digested in the stomach.

Solubility in water can be expressed as the amount of water required to completely dissolve 1 mg of a material at room temperature and one atmosphere of pressure. A material or solute is considered highly water soluble if 1 ml of water can dissolve 1 mg of solute and result in a clear solution that is miscible with water. Several techniques have sought to increase the water solubility of cannabinoids so that they can be absorbed more rapidly by mucosal membranes especially those in the mouth. These techniques include dissolving cannabinoids in water miscible organic solvents such as ethanol, the use of surfactant micelles to form cannabinoid emulsions and use of chelating agents. Although effective, each of these techniques has its limitations ranging from discomfort to toxicity.

Another approach to increasing cannabinoid water solubility is the derivatization of cannabinoid molecules by substituting functional groups. For example, esterification of the phenolic oxygen at carbon 1 in THC$\Delta$9 allows attachment of nitrogen containing heterocyclic rings. Heterocyclic rings known in the art include piperidine, piperazine, and alkyl substituted amino moieties. These cannabinoid esters readily form hydrochloride salt and are very soluble in water. Another modification known in the art is substitution of the THC$\Delta$9 pentyl sidechain at carbon 3 by addition of a nitrogenous or azole moiety including imidazole, pyrozole, and triazaole. THC$\Delta$9 side chain modifications and combinations of both 1 and 3 carbon derivatizations result in very water soluble cannabinoids. Many derivatized cannabinoid molecules are believed to retain pharmacological activity and therefore presumably also retain the ability to bind to endogenous mammalian cannabinoid receptors CB1 and CB2. Given that virtually all of the best known cannabinoids contain phenolic oxygen atoms and pentyl side chains these derivatization techniques may be applied to all of them for the purpose of increasing water solubility.

Compared to cannabinoids, terpenoids are a much broader class of molecules that are found ubiquitously in plants. Terpenoids also have much broader therapeutic effects including antacid, analgesic, anti-inflammatory, and anti-anxiety properties which extend well beyond the effects of cannabinoids alone. Terpenoids therefore present similar opportunities for derivatizations that increase water solubility and speed of effect.

The invention described herein is directed to the application of said water soluble cannabinoid and terpenoid molecules in the preparation of orally administered cannabis compositions. Said orally administered cannabis compositions will offer precise and reliable dosing as well as fast action resulting from rapid absorption into blood through oral mucosa.

RELEVANT ART

Russo E B. Taming THC: potential cannabis synergy and phytocannabinoid-terpenoid entourage effects. British Journal of Pharmacology. 2011; 163(7):1344-1364. doi:10.1111/j.1476-5381.2011.01238.x.

Hyo Min Park, Ji Hae Lee, Jia Yaoyao, Hee Jin Jun, Sung Joon Lee, Limonene, a natural cyclic terpene, is an agonistic ligand for adenosine A2A receptors, Biochemical and Biophysical Research Communications, Volume 404, Issue 1, 2011, Pages 345-348,ISSN 0006-291X, https://doi.org/10.1016/j.bbrc.2010.11.121.

Juha Juntunen, Juhani Huuskonen, Krista Laine, Riku Niemi, Hannu Taipale, Tapio Nevalainen, David W Pate, Tomi Järvinen, Anandamide prodrugs: 1. Water-soluble phosphate esters of arachidonylethanolamide and R-methanandamide, European Journal of Pharmaceutical Sciences, Volume 19, Issue 1, 2003, Pages 37-43, ISSN 0928-0987, https://doi.org/10.1016/50928-0987(03)00044-7.

Atmaram D Khanolkar, Sonya L Palmer, Alexandros Makriyannis, Molecular probes for the cannabinoid receptors, Chemistry and Physics of Lipids, Volume 108, Issues 1-2, 2000, Pages 37-52, ISSN 0009-3084,https://doi.org/10.1016/S0009-3084(00)00186-9.

U.S. Pat. No. 9,526,792, Degeeter, Composition and Method for Producing an Edible Base Product-discloses a composition comprising cannabis concentrate, starch concentrate containing tapioca maltodextrin, a rice concentrate, and a lipid concentrate containing lecithin.

U.S. Pat. No. 8,906,429, Kolsky, Medical Cannabis Lozenges and Compositions Thereof-discloses formulating a hydrophilic mixture of cannabinoids, sugar, corn syrup, xylitol, purified water, organic flavorings, coconut oil.

U.S. Pat. No. 7,025,992, Whittle et al., Pharmaceutical Formulations-discloses pharmaceutical formulations for use in administration of a lipophilic medicament via a mucosal surface which upon hydration form an emulsion containing the lipophilic medicament which is capable of adhering to a mucosal surface and allowing controlled release of the medicament.

U.S. Pat. No. 6,328,992, Brooke et al., Cannabinoid Patch and Method for Cannabis Transdermal Delivery-discloses a patch containing cannabis materials in the presence of permeation enhancers and cannabis carriers.

U.S. Pat. No. 6,132,762, Cristobal, Transcutaneous Application of Marijuana-discloses a formulation comprising marijuana and a topical transcutaneous carrier selected from the group consisting of water, alcohol, aldehyde, ketone, carboxylic acid, mineral oil and dimethyl sulfoxide.

U.S. Pat. No. 5,847,128, Martin et al., Water Soluble Derivatives of Cannabinoids-discloses water-soluble esters of tetrahydrocannabinoids which are well suited for administration in therapeutic aqueous formulations.

US 2017/0020945, Riello et al., Food and Beverage Compositions Infused with Lipophilic Active Agents and Methods of Use Thereof-discloses food and beverage compositions infused with lipophilic active agents such as cannabinoids, nicotine, nonsteroidal anti-inflammatory (NSAIDs), and vitamins that provide enhanced bioavailability of the lipophilic active agents in a subject and that makes the unpleasant taste of lipophilic active agents.

US 2016/0296464A1, Lindsay, Sublingual Cannabis Dosage Form and Method of Making and Using the Same-discloses use of decarboxylated cannabis in a fiber dispenser also containing wax and flavorants.

US 2016/0199299 A1, Uren-Cannabis Infused Chewing Composition-discloses a quantity of cannabis plant matter, a quantity of cannabis extract, a quantity of bonding composition, a quantity of moisturizer, and a quantity of flavor enhancer.

US 2014/0271940 A1, Wurzer, Bioactive Concentrates and Uses Thereof-discloses concentrates obtained from cannabis for use in edible matrices and nutraceuticals.

US 2008/0064679 A1, Martin, Water Soluble Cannabinoids-discloses cannabinoids that are made water soluble by derivatization of the alkyl side chain and or the phenolic hydroxyl group of tetrahydrocannabinol.

US 2004/0138293 A1, Werner, Pharmaceutical Composition Made of Cannabis Extracts-discloses a preparation composed of concentrated THC and CBD, with a suitable lipophilic solvents or suspension carriers.

SUMMARY OF THE INVENTION

The present invention provides compositions of orally administered cannabinoids and terpenoids and methods of making the same.

An object of the present invention is to provide an orally administered cannabis product with precise and reliable dosage.

An object of the present invention is to provide an orally administered cannabis product with fast action.

An object of the present invention is to provide an orally administered cannabis product whose effects can be felt by the consumer within a few minutes.

An object of the present invention is to provide an orally administered cannabis product whose effects can be felt by the consumer after an hour or more.

An object of the present invention is to provide an orally administered cannabis product whose effects can be felt by the consumer both quickly and for an hour or more.

An object of the present invention is to provide an orally administered cannabis product that may be safely ingested.

An object of the present invention is to provide an orally administered cannabis product comprised of water soluble cannabinoid molecules.

Non-limiting examples of the cannabinoids that may be derivatized to increase water solubility are chosen from the group including but not limited to CBG (Cannabigerol), CBC (Cannabichromene), CBL (Cannabicyclol), CBV (Cannabivarin), THCV (Tetrahydrocannabivarin); CBDV (Cannabidivarin); CBCV (Cannabichromevarin); CBGV (Cannabigerovarin); CBGM (Cannabigerol Monomethyl Ether); THC (Tetrahydrocannabinol); THCA (Tetrahydrocannbinolic acid); CBD (Cannabidiol); CBDA (Cannabidiolic Acid) and isomers and enantiomers thereof.

An object of the present invention is to provide an orally administered cannabis product comprised of water soluble terpene and terpenoid molecules.

Non-limiting examples of the terpene and terpenoids that may be derivatized to increase water solubility are chosen from the group including but not limited to pinene, linalool, mycrene, limonene, ocimene, terpinolene, terpineol, valencene, beta Caryophyllen, geraniol, humulene, phellandrene, careen, terpinene, fenchol, borneol, bisabolol, phytol, camphene, sabinene, camphor, isoborneol, menthol, cedrene, nerolidol, guaiol, isopulegol, cymene, geranyl acetate, eucalyptol, pulegone. and isomers and enantiomers thereof.

An object of the present invention is to provide an orally administered cannabis product comprised of water soluble cannabinoid and terpenoid molecules prepared from organic synthesis.

An object of the present invention is to provide an orally administered cannabis product comprised of water soluble cannabinoid and terpenoid molecules prepared from fermentation by recombinant microorganisms.

An object of the present invention is to provide an orally administered cannabis product comprised of water soluble cannabinoid and terpenoid molecules prepared from extraction of cannabis flowers.

An object of the present invention is to provide an orally administered cannabis product wherein said water soluble cannabinoids and terpenoids may be derivatized by phenolic esterification.

An object of the present invention is to provide an orally administered cannabis product wherein said water soluble cannabinoid and terpenoids may be derivatized by pentyl side chain substitution.

An object of the present invention is to provide an orally administered cannabis product wherein said water soluble cannabinoids and terpenoids may be derivatized by methods known in the art.

An object of the present invention is to provide an orally administered cannabis product wherein water soluble cannabinoids and terpenoids may be combined with non-derivatized cannabinoids and terpenoids in any useful ratios yielding complex effects.

An object of the present invention is to provide an orally administered cannabis product that may also be comprised of nicotine.

An object of the present invention is to provide an orally administered cannabis product that is disposed upon a fibrous carrier. Non limiting examples of fibrous carriers are chosen from the group including but not limited to coconut coir, hemp, rice, bamboo, corn husk, silk husk, fruit skin, straw, flax, soy, synthetic fibers, and animal fibers.

An object of the present invention is to provide an orally administered cannabis product that is disposed within in a pouch. Non-limiting examples of pouch materials are chosen from the group including but not limited to cellulose, other plant based fiber, animal fibers, nylon, synthetic fibers and nanofibers.

An object of the present invention is to provide an orally administered cannabis product that may be disposed within a carrier oil. Non-limiting examples of carrier oils are chosen from the group including but not limited to medium chain triglycerides (MCT) oil, apricot oil, grape seed oil, avocado oil, olive oil, sesame oil, evening primrose oil, rapeseed oil, camellia seed oil, sunflower oil, marula oil, jojoba oil, emu oil, castor oil, borage seed oil, walnut oil, peanut oil, pecan oil, macadamia oil, coconut oil, palm oil, hazelnut oil, cocoa butter and almond oil.

An object of the present invention is to provide an orally administered cannabis product that is composed of binding agents. Non-limiting examples of binding agents are chosen from the group including but not limited to xanathan gum, guar gum, agar, gelatin, pectin, psyllium husk powder, flax, and chia seed.

An object of the present invention is to provide an orally administered cannabis product that is composed of flavoring agents. Non-limiting examples of flavoring agents are chosen from the group including but not limited to monk fruit (*Siraitia grosvenorii*), monk fruit substitutes, monk fruit derivatives, monk fruit relatives, xylitol, other sugar alcohols, stevia extracted from the leaves of the plant species *Stevia rebaudiana*, stevia related sweeteners, miracle fruit (*Synsepalum dulcificum*), miracle fruit related sweeteners, citric acid, other organic acids used in food production, cayenne pepper, salt, and sodium bicarbonate.

An object of the present invention is to provide an orally administered cannabis product that is composed of essential oils. Non-limiting examples of essential oils are chosen from the group including but not limited to: wintergreen, peppermint, spearmint, corn mint, mandarin, orange, grapefruit, lime, lemon, apple, strawberry, tangerine, ginger, lavender, cinnamon bark oil, cinnamon leaf oil, pineapple fragrance oil and tobacco oil.

An object of the present invention is to provide an orally administered cannabis product that is composed of vitamins. Non-limiting examples supplements are chosen from the group consisting of but not limited to coenzyme-Q10, pyrroloquinoline quinone, nicotinamide riboside, vitamin C, methylcobalamin (vitamin B12), pyridoxal-5-phosphate (p5p), 1-theanine, caffeine, rhodiola rosea, choline, pine pollen extract, deer antler velvet, gingko biloba, vinpocetine, bacopa monnieri, ganoderman lucidium (reishi mushroom), cordyceps sinesis (cordyceps mushroom), hericium erinaceus (lions mane mushroom), creatine monohydrate, branched chain amino acids (bcaa's), guarana seed extract, panax ginseng root extract, sibering ginseng root extract, ashwaghanda, astralagus, curcurmin, maca, holy basil, schisandra, tongkat ali, GABA (gamma aminobutyric acid), tribulus terrestris.

An object of the present invention is to provide an orally administered cannabis product that is composed of emulsifiers. Non-limiting examples of emulsifiers are chosen from the group consisting of but not limited to lecithin, mustard, sodium phosphates, sodium stearoyl lactylate, polysorbates oleates, stearates, and other esters of monoglycerides of fatty acids, and mono- and diglycerides of fatty acids The present invention achieves its objects by providing compositions for an orally administered cannabis product and methods for making the same. The manners in which the invention achieves its objects and other objects which are inherent in the invention will become more readily apparent when reference is made to the detailed description of the invention.

DETAILED DESCRIPTION OF THE INVENTION

Various embodiments of the invention are described in detail and may be further illustrated by the provided examples. As used in the description herein and throughout the claims that follow, the meaning of "a," "an," and "the" includes the plural reference unless the context clearly dictates otherwise. Also, as used in the description herein, the meaning of "in" includes "in" and "on" unless the context clearly dictates otherwise.

Throughout this specification and claims, the word "comprise," or variations such as "comprises" or "comprising" will be understood to imply the inclusion of a stated integer or group of integers but not the exclusion of any other integer or group of integers.

Terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms does not exclude the use of other synonyms. The use of examples anywhere in this specification, including examples of any terms discussed herein, is illustrative only, and in no way limits the scope of the invention so long as the data are processed, sampled, converted, or the like according to the invention without regard for any particular theory or scheme of action. The entire contents of all the references (including literature references, issued patents, published patent applications, and co-pending patent applications) cited throughout this application are hereby expressly incorporated by reference.

EXAMPLE 1

In an embodiment, an orally administered cannabinoid and terpenoid composition may be prepared according to the following procedure. Fat soluble ingredients including 15 parts vegetable glyercine, 15 parts coconut oil, and 1.5 parts orange essential oil are combined over medium heat with stirring. To this preparation is added 10 parts non derivatized D-limonene extracted and purified from cannabis flowers in a liquid preparation at 100 mg/ml.

Water soluble ingredients are combined in a separate container over medium heat with stirring as follows, 5 parts citric acid, 5 parts concentrated fruit flavoring, and 10 parts fine sugar. When fully dissolved and mixed, 10 parts esterified THCΔ9 derived from organic synthesis and present in a liquid preparation at 100 mg/ml is added to the solution. Once the water soluble components are thoroughly mixed they are slowly combined with a solution of lecithin representing 5 parts of the final preparation.

When the water soluble and lecithin components are thoroughly combined the fat soluble portion is then slowly added with aggressive mixing in order to produce a fine highly stable emulsion. Once the emulsion reaches stability it is ready to be added to an automatic mixer containing the dry ingredients.

The dry ingredients include 20 parts finely ground, steam sterilized coconut coir fibers and 0.5 parts ginseng root extract powder. The emulsion is slowly added to the dry ingredients and mixed on high speed for a period of 10 minutes. Lastly, 3 parts xanathan gum is added to the mixer and the preparation mixed on medium speed for another hour. The resulting preparation is then added to a pouching machine and dispensed to cellulose fiber pouches in 1 g allotments containing 10 mg water soluble THCΔ9 and 10 mg D-limonene.

EXAMPLE 2

In another embodiment it is preferable to significantly reduce oil used in the orally administered cannabinoid and terpenoid composition which may be may be prepared according the following procedure. The following components, 40 parts concentrated mint flavoring, 1 part co-enzymeQ10, 10 parts Eucalyptol, 10 parts ester derivatized CBD prepared as a hydrochloride salt, and 10 parts pentyl side chain derivatized Cannabichromene also prepared as a hydrochloride salt, are combined over gentle heating in an aqueous solution. When the components are fully dissolved into solution they are added to an automatic mixer containing 20 parts finely ground corn husk fiber. The combined ingredients are mixed at high speed for 5 minutes and then 9 parts of agar is added to the mixture and it is mixed for another 30 minutes. The resulting preparation is then added a pouching machine and dispensed to animal fiber pouches in 1 g allotments containing 100 mg CBD, 100 mg CBC and 100 mg Eucalyptol.

EXAMPLE 3

In yet another embodiment it may be preferable to more accurately control dosing by adding the cannabinoid and terpenoid concentrates to the composition following the packaging step. In this embodiment the following components, 30 parts concentrated cinnamon flavoring and 10 parts caffeine, 10 parts nicotine oil are combined over gentle heating in a dilute alcohol solution. After the components are fully combined they are added to an automatic mixer containing 20 parts finely ground hemp fiber. The combined ingredients are mixed at high speed for 5 minutes and then 10 parts gelatin is added to the mixture and it is then mixed for another 30 minutes. The resulting preparation is then added a pouching machine and dispensed to nylon fiber pouches in 1 g allotments. The finished pouches are gently dehydrated and then positioned so that each may be treated with a quantity of water soluble cannabinoid and terpenoid concentrate in liquid form. Next 10 parts Nerolidol in a liquid preparation of 100 mg/ml and 10 parts pentyl side chain derivatized THCΔ8 also in a liquid preparation at 100 mg/ml are added to each pouch by dropper and allowed to air dry for 1 hour. The finished pouches are then ready for packaging and distribution.

It will be understood that various modifications can be made to the various embodiments of the present invention herein disclosed without departing from the spirit and scope thereof. Therefore, the above description should not be construed as limiting the invention, but merely as an exemplification of embodiments thereof. Those of skill in the art will envision other modifications within the scope and sprit of the present invention as defined by the claims appended hereto.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed:
1. A product for oral administration of cannabinoids comprising:
    a cannabinoid, wherein if the cannabinoid is a water soluble cannabinoid it is chosen from the group consisting of derivatized carbon 1 phenolic esters and derivatized carbon 3 pentyl side chains;
    a terpene chosen from the group consisting of pinene, linalool, mycrene, limonene, ocimene, terpinolene, terpinol, valencene, beta Caryophyllen, geraniol, humulene, phellandrene, careen, terpinene, fenchol, borneol, bisabolol, phytol, camphene, sabinene, camphor, isoberneol, menthol, cedrene, nerolidol, guaiol, isopulegol, cymene, geranyl acetate, eucalyptol, pulegone, and isomers and enantiomers thereof;
    a fibrous carrier chosen from the group consisting of: coconut coir, hemp, rice, bamboo, corn husk, silk husk, fruit skin, straw, flax, soy, synthetic fibers, and animal fibers;
    one or a combination of carrier oils chosen from the group consisting of medium chain triglycerides (MCT) oil, apricot oil, grape seed oil, avocado oil, olive oil, sesame oil, evening primrose oil, rapeseed oil, camellia seed oil, sunflower oil, marula oil, jojoba oil, emu oil, castor oil, borage seed oil, walnut oil, peanut oil, pecan oil, macadamia oil, coconut oil, palm oil, hazelnut oil, cocoa butter and almond oil;
    one or a combination of essential oils chosen from the group consisting of wintergreen, peppermint, spearmint, corn mint, mandarin, orange, grapefruit, lime, lemon, apple, strawberry, tangerine, ginger, lavender, cinnamon bark oil, cinnamon leaf oil, pineapple fragrance oil and tobacco oil;
    one or a combination of flavorings chosen from the group consisting of monk fruit (Siraitia grosvenorii), monk fruit substitutes, monk fruit derivatives, monk fruit relatives, xylitol, other sugar alcohols, stevia extracted from the leaves of the plant species Stevia rebaudiana, stevia related sweeteners, miracle fruit (Synsepalum dulcificum), miracle fruit related sweeteners, citric acid, other organic acids used in food production, cayenne pepper, salt, and sodium bicarbonate;
    one or a combination of binding agents chosen from the group consisting of xanathan gum, guar gum, agar, gelatin, pectin, psyllium husk powder, flax, and chia seed; and
    a pouch made from a material chosen from the group consisting of cellulose, other plant based fiber, animal fibers, nylon, synthetic fibers and nanofibers.
2. A product for oral administration of cannabinoids comprising:
    a cannabinoid, wherein if the cannabinoid is a water soluble cannabinoid it is chosen from the group consisting of derivatized carbon 1 phenolic esters and derivatized carbon 3 pentyl side chains;

a terpene chosen from the group consisting of pinene, linalool, mycrene, limonene, ocimene, terpinolene, terpineol, valencene, beta Caryophyllen, geranoil, humulene, phellandrene, careen, terpinene, fenchol, borneol, bisabolol, phytol, camphene, sabinene, camphor, isoborneol, menthol, cedrene, nerolidol, guaiol, isopulegol, cymene, geranyl acetate, eucalyptol, pulegone, and isomers and enantiomers thereof;

a fibrous carrier chosen from the group consisting of: coconut coir, hemp, rice, bamboo, corn husk, silk husk, fruit skin, straw, flax, soy, synthetic fibers, and animal fibers;

one or a combination of carrier oils chosen from the group consisting of medium chain trigylcerides (MCT) oil, apricot oil, grape seed oil, avocado oil, olive oil, sesame oil, evening primrose oil, rapeseed oil, camellia seed oil, sunflower oil, marula oil, jojoba oil, emu oil, castor oil, borage seed oil, walnut oil, peanut oil, pecan oil, macadamia oil, coconut oil, palm oil, hazelnut oil, cocoa butter and almond oil;

one or a combination of essential oils chosen from the group consisting of wintergreen, peppermint, spearmint, corn mint, mandarin, orange, grapefruit, lime, lemon, apple, strawberry, tangerine, ginger, lavender, cinnamon bark oil, cinnamon leaf oil, pineapple fragrance oil and tobacco oil;

one or a combination of flavorings chosen from the group consisting of monk fruit (Siraitia grosvenorii), monk fruit substitutes, monk fruit derivatives, monk fruit relatives, xylitol, other sugar alcohols, stevia extracted from the leaves of the plant species Stevia rebaudiana, stevia related sweeteners, miracle fruit (Synsepalum dulcificum), miracle fruit related sweeteners, citric acid, other organic acids used in food production, cayenne pepper, salt, and sodium bicarbonate;

one or a combination of binding agents chosen from the group consisting of xanathan gum, guar gum, agar, gelatin, pectin, psyllium husk powder, flax, and chia seed;

one or a combination of emulsifiers chosen from the group consisting of lecithin, mustard, sodium phospates, sodium stearoyl lactylate, polysorbates oleates, stearates, and other esters of monoglycerides of fatty acids, and mono- and diglycerides of fatty acids; and a pouch made from a material chosen from the group consisting of cellulose, other plant based fiber, animal fibers, nylon, synthetic fibers and nanofibers.

3. A product for oral administration of cannabinoids comprising:

a cannabinoid, wherein if the cannabinoid is a water soluble cannabinoid it is chosen from the group consisting of derivatized carbon 1 phenolic esters and derivatized carbon 3 pentyl side chains;

a terpene chosen from the group consisting of pinene, linalool, mycrene, limonene, ocimene, terpinolene, terpineol, valencene, beta Caryophyllen, geranoil, humulene, phellandrene, careen, terpinene, fenchol, borneol, biabolol, phytol, camphene, sabinene, camphor, isoborneol, menthol, cedrene, nerolidol, guaiol, isopulegol, cymene, geranyl acetate, eucalyptol, pulegone, and isomers and enantiomers thereof;

a fibrous carrier chosen from the group consisting of: coconut coir, hemp, rice, bamboo, corn husk, silk husk, fruit skin, straw, flax, soy, synthetic fibers, and animal fibers;

one or a combination of carrier oils chosen from the group consisting of medium chain triglycerides (MCT) oil, apricot oil, grape seed oil, avocado oil, olive oil, sesame oil, evening primrose oil, rapeseed oil, camellia seed oil, sunflower oil, marula oil, jojoba oil, emu oil, castor oil, borage seed oil, walnut oil, peanut oil, pecan oil, macadamia oil, coconut oil, palm oil, hazelnut oil, cocoa butter and almond oil;

one or a combination of essential oils chosen from the group consisting of wintergreen, peppermint, spearmint, corn mint, mandarin, orange, grapefruit, lime, lemon, apple, strawberry, tangerine, ginger, lavender, cinnamon bark oil, cinnamon leaf oil, pineapple fragrance oil and tobacco oil;

one or a combination of flavorings chosen from the group consisting of monk fruit (Siraitia grosvenorii), monk fruit substitutes, monk fruit derivatives, monk fruit relatives, xylitol, other sugar alcohols, stevia extracted from the leaves of the plant species Stevia rebaudiana, stevia related sweeteners, miracle fruit (Synsepalum dulcificum), miracle fruit related sweeteners, citric acid, other organic acids used in food production, cayenne pepper, salt, and sodium bicarbonate;

one or a combination of binding agents chosen from the group consisting of xanathan gum, guar gum, agar, gelatin, pectin, psyllium husk powder, flax, and chia seed; and a pouch made from a material chosen from the group consisting of cellulose, other plant based fiber, animal fibers, nylon, synthetic fibers and nanofibers;

one or a combination of emulsifiers chosen from the group consisting of lecithin, mustard, sodium phosphates, sodium stearoyl lactylate, polysorbates oleates, stearates, and other esters of monoglycerides of fatty acids, and mono- and diglycerides of fatty acids;

one or a combination of vitamins chosen from the group consisting of coenzyme-Q10, pyrroloquinoline quinone, nicotinamide riboside, vitamin C, methylcobalamin (vitamin B12), pyridoxal-5-phosphate (p5p), 1-theanine, caffeine, rhodiola rosea, choline, pine pollen extract, deer antler velvet, gingko biloba, vinpocetine, bacopa monnieri, ganoderman lucidium (reishi mushroom), cordyceps sinesis (cordyceps mushroom), hericium erinaceus (lions mane mushroom), creatine monohydrate, branched chain amino acids (bcaa's), guarana seed extract, panax ginseng root extract, sibering ginseng root extract, ashwaghanda, astralagus, curcurmin, maca, holy basil, schisandra, tongkat ali, GABA (gamma aminobutyric acid), and tribulus terrestris; and a pouch made from a material chosen from the group consisting of cellulose, other plant based fiber, animal fibers, nylon, synthetic fibers and nanofibers.

4. The product of claim 3 further comprising a nicotine component.

5. The product of claim 1, further comprising a nicotine component.

6. The product of claim 2, further comprising a nicotine component.

* * * * *